United States Patent [19]
Sato et al.

[11] Patent Number: 4,992,610
[45] Date of Patent: Feb. 12, 1991

[54] DIMERIZATION OF LOWER α-OLEFINS

[75] Inventors: Hiroshi Sato, Niihama; Kenshi Uchida, Takatsuki; Hideto Tojima, Kyoto, all of Japan

[73] Assignee: Sumitomo Chemical Company, Limited, Osaka, Japan

[21] Appl. No.: 316,945

[22] Filed: Feb. 28, 1989

[30] Foreign Application Priority Data

Feb. 29, 1988 [JP] Japan .................. 63-47860

[51] Int. Cl.$^5$ .............................. C07C 2/26; C07C 2/24
[52] U.S. Cl. ................................ 585/511; 585/512; 585/513
[58] Field of Search ................ 585/511, 512, 513

[56] References Cited

U.S. PATENT DOCUMENTS

| | | | |
|---|---|---|---|
| 4,155,946 | 5/1979 | Sato et al. ............... | 585/513 |
| 4,311,613 | 1/1982 | Pellegrini et al. . | |
| 4,476,341 | 10/1984 | Mathys ................... | 585/513 |
| 4,482,640 | 11/1984 | Knudsen et al. . | |
| 4,709,112 | 11/1987 | Sato et al. . | |

FOREIGN PATENT DOCUMENTS

| | | |
|---|---|---|
| 0231748 | 8/1987 | European Pat. Off. . |
| 2021523 | 2/1971 | Fed. Rep. of Germany . |
| 2062293 | 6/1971 | Fed. Rep. of Germany . |
| 2828577 | 1/1979 | Fed. Rep. of Germany . |
| 1547921 | 4/1968 | France . |
| 57-167932 | 10/1982 | Japan . |

OTHER PUBLICATIONS 47-22807 pp. 33–35, Toray Inds. Inc., Derwent Publications Ltd.

Chemical Abstracts "Dimerization of Lower α-Olefins" Sumitomo Chemical Co., Ltd. p. 506.

Primary Examiner—H. M. S. Sneed
Assistant Examiner—J. Saba
Attorney, Agent, or Firm—Birch, Stewart, Kolasch & Birch

[57] ABSTRACT

A dimer of a lower α-olefin is prepared by dimerizing a lower α-olefin in the presence of a catalyst comprising
(A) nickel chloride,
(B) a trialkylaluminum
(C) at least one phosphorus compound selected from the group consisting of compounds of the formulae:

$$PR^1R^2R^3 \qquad \text{(I)}$$

$$P(NR^1{}_2)_3 \qquad \text{(II)}$$

and $$P(OR^1)_3 \qquad \text{(III)}$$

wherein $R^1$, $R^2$ and $R^3$ are the same or different and each an alkyl group, a cycloalkyl group or a phenyl group and
(D) 1,1,1,3,3,3-hexafluoroisopropanol, wherein the catalyst has improved activity because of the use of nickel chloride as a nickel component, so that the amounts of expensive trialkylaluminum and hexafluoroisopropanol can be decreased and the cost of the catalyst can be significantly reduced.

14 Claims, No Drawings

DIMERIZATION OF LOWER α-OLEFINS

BACKGROUND OF THE INVENTION

1. Field of the Invention

The present invention relates to a process for dimerization of a lower α-olefin. More particularly, the present invention relates to a process for dimerization of a lower α-olefin which uses a novel nickel-containing Ziegler catalyst.

2. Description of the Related Art

Dimers of lower α-olefins such as ethylene, propylene, butene, etc., are useful as basic compounds in the production of agricultural chemicals, perfumes and other chemicals or as monomers for the production of polymers. Some of the known processes for the preparation of the dimers of lower α-olefin comprise dimerization of the -olefin in the presence of a nickel-containing Ziegler catalyst.

For example, Japanese Patent Kokai Publication No. 167932/1982 discloses a catalyst comprising a nickel salt, a trialkylaluminum, an organic phosphine, a halogenated phenol and water. When the α-olefin is dimerized in the presence of such a catalyst, in some cases, a small amount of precipitates may be formed in the reaction system, which results in reduction of cooling efficiency of a heat exchanger for cooling the reaction system.

It was proposed to use a catalyst comprising a nickel salt of an organic acid, a trialkylaluminum, an organic phosphine and fluorinated isopropanol (cf. Japanese Patent Kokai Publication No. 158225/1987).

SUMMARY OF THE INVENTION

One object of the present invention is to provide a nickel-containing Ziegler catalyst which effectively catalyzes the dimerization the of lower α-olefins.

Another object of the present invention is to provide a process for dimerization of the lower α-olefins.

These and other objects of the present invention are accomplished by a novel nickel-containing Ziegler. catalyst comprising nickel chloride, a trialkylaluminum, a phosphorus compound and 1,1,1,3,3,3-hexafluoroisopropanol.

Accordingly, the present invention provides a process for preparing a dimer of a lower α-olefin comprising dimerizing the lower α-olefin in the presence of a catalyst comprising
(A) nickel chloride,
(B) a trialkylaluminum
(C) at least one phosphorus compound selected from the group consisting of compounds of the formulae:

$$PR^1R^2R^3 \qquad (I)$$

$$P(NR^1{}_2)_3 \qquad (II)$$

and $$P(OR^1)_3 \qquad (III)$$

wherein $R^1$, $R^2$ and $R^3$ are the same or different and each an alkyl group, a cycloalkyl group or a phenyl group,
(D) 1,1,1,3,3,3-hexafluoroisopropanol, and optionally (E) at least one active hydrogen-containing compound of the formula:

$$R-OH \qquad (IV)$$

wherein R is a hydrogen atom, an alkyl group, an allyl group, an aryl group or an acyl group in an amount less than the equimolar amount to the trialkylaluminum.

DETAILED DESCRIPTION OF THE INVENTION

The Ziegler catalyst of the present invention is characterized in the use of nickel chloride as a nickel-containing component. Nickel chloride to be contained in the Ziegler catalyst of the present invention may be in the form of an anhydrous salt or a hydrated salt.

Specific examples of the trialkylaluminum (B) are trimethylaluminum, triethylaluminum, tri-n-propylaluminum, tri-isopropylaluminum, tri-n-butylaluminum, tri-isobutyl-aluminum, tri-n-pentylaluminum, tri-n-hexylaluminum, tri-cyclohexylaluminum, etc.

The molar amount of the trialkylaluminum is usually 2 to 500 times, preferably 2 to 100 times, more preferably 2 to 10 times the amount of nickel chloride (A).

Specific examples of the organic phosphine compound (I) which is one of the trivalent phosphorus compounds (C) are trimethylphosphine, triethylphosphine, tri-n-propylphosphine, tri-isopropylphosphine, tri-n-butylphosphine, tri-isobutylphosphine, tri-tert.-butylphosphine, tri-sec.butylphosphine, tricyclopropylphosphine, tricyclohexylphosphine, triphenylphosphine, tri-p-tolylphosphine, tri-p-methoxyphenylphosphine, tri-2,4,6-trimethylphenylphosphine, phenyl-di-isopropylphosphine, ethyl-di-isopropylphosphine, ethyl-di-tert.-butylphosphine, ethyl-dicyclohexylphosphine, methylpropylphenylphosphine, methylphenylbenzylphosphine, etc.

Specific examples of the aminophosphine compound (II) are tris-dimethylaminophosphine, tris-diethylaminophosphine, tris-di-n-propylaminophosphine, tris-di-iso-propylaminophosphine, tris-di-n-butylaminophosphine, tris-di-isobutylaminophosphine, tris-di-tert.-butylaminophosphine, tris-dicyclohexylaminophosphine, etc.

Specific examples of the phosphite (III) are trimethylphosphite, triethylphosphite, tri-n-propylphosphite, tri-isopropylphosphite, tri-n-butylphosphite, tri-isobutylphosphite, tri-tert.-butylphosphite, tricyclohexylphosphite, triphenylphosphite, tri-p-tolylphosphite, tri-p-methoxyphenylphosphite, etc.

Among the components (A) to (D) of the catalyst, the trivalent phosphorus compound (C) has the largest influence on the isomer distribution of the α-olefin dimers. For example, when 2,3-dimethylbutenes are to be prepared in high yields by dimerization of propylene, organic phosphines such as tri-isopropylphosphine, tricyclohexylphosphine, tri-sec.-butylphosphine, etc., are preferably used.

The molar amount of the phosphorus compound (C) is usually 0.1 to 50 times, preferably 0.1 to 20 times, more preferably 0.1 to 2 times the amount of nickel chloride (A).

1,1,1,3,3,3-Hexafluoroisopropanol (D) is one of the essential components of the Ziegler catalyst having the dimerization activity according to the present invention. Without 1,1,1,3,3,3-hexafluoroisopropanol, the catalyst has substantially no dimerization activity. Through variation of the amount of 1,1,1,3,3,3-hexafluoroisopropanol, the isomer distribution of the double bond in the olefin dimer can be controlled. For example, when the 2,3-dimethylbutenes are selectively prepared, 2,3-dimethylbutene-1 is obtained if the amount of 1,1,1,3,3,3-hexafluoroisopropanol is small, while 2,3-dimethylbutene-2 is obtained if the amount of 1,1,1,3,3,3-hexafluoroisopropanol is increased.

The molar amount of 1,1,1,3,3,3-hexafluoroisopropanol is 0.2 to 10 times, preferably 0.5 to 5 times, more preferably 1 to 4 times the amount of the trialkylaluminum (B).

In addition to the above essential components, the Ziegler catalyst of the present invention may comprise the active hydrogen-containing compound (E) of the formula (IV). Thereby, the isomer distribution of the olefin dimer can be varied. For example, in case of dimerization of propylene, the catalyst comprising the active hydrogen-containing compound (E) will increase the selectivity of 2,3-dimethyl-butene-1, 2,3-dimethyl-butene-2 and the like.

Specific examples of the active hydrogen-containing compound (IV) are water, lower alkyl alcohols (e.g. methanol, ethanol, n-propanol, isopropanol, n-butanol, tert.-butanol, amyl alcohol, hexanol, heptanol, octanol, etc.), allyl alcohol, phenols (e.g. phenol, cresol, xylenol, etc.) and carboxylic acids, (e.g. acetic acid, propionic acid, etc.). Among them, water, methanol, ethanol, n-propanol, octanol, allyl alcohol, phenol, acetic acid and mixtures thereof are preferred.

The molar amount of the compound (E) is less than equimolar to, preferably 0.1 to 0.8 time, more preferably 0.2 to 0.6 time the amount of the trialkylaluminum (B).

Although the catalyst system of the present invention can be stably used in the presence of the lower α-olefin to be dimerized during the preparation step, the catalyst is preferably prepared in the presence of a linear conjugated diolefin as a stabilizing aid. Examples of such conjugated diolefin are butadiene, isoprene and 1,3-pentadiene. The molar amount of the conjugated diolefin is not more than 200 times the amount of nickel chloride (A). Excessive use of the conjugated diolefin does not improve the stabilizing effect.

The components (A) to (D) may be mixed in any order. Preferably, nickel chloride (A), the trivalent phosphorus compound (C), the trialkylaluminum (B) and 1,1,1,3,3,3-hexafluoroisopropanol (D) are added in this order [(A), (C), (B) and (D)] in the presence of a small amount of α-olefin or the conjugated diolefin as the stabilizing aid. When the optional component (E) is used, the components are added in the sequence of (A), (C), (B), (E) and (D).

In general, the catalyst is prepared in an inert solvent. Examples of such solvent are aromatic hydrocarbons (e.g. benzene, toluene, xylene, etc.), aliphatic hydrocarbons (e.g. hexane, heptane, cyclohexane, etc.) and halogenated aromatic hydrocarbons (e.g. chlorobenzene, dichlorobenzene, etc.). Among them, the aromatic hydrocarbons and the halogenated aromatic hydrocarbons are preferred.

The catalyst is prepared usually at a temperature of $-80°$ C. to $+60°$ C., preferably $-20°$ C. to $+40°$ C.

In some cases, the catalyst may be prepared in the liquid or liquefied α-olefin.

The concentration of the catalyst during the dimerization is usually from $10^{-5}$ to $10^{-1}$ mol/liter in terms of the concentration of the nickel component. The reaction temperature for dimerization is usually from $-80°$ C. to $+60°$ C., preferably from $-21°$ C. to $+40°$ C. The reaction pressure is from atmospheric pressure to autogenous equilibrium pressure at the reaction temperature.

Examples of the lower α-olefin to be dimerized according to the present invention are those having at least 2, preferably 2 to 4 carbon atoms such as ethylene, propylene, 1-butene, etc.

After the dimerization reaction, the reaction is stopped and the catalyst is separated from the reaction mixture by per se conventional manners. Then, the reaction mixture is rectified to obtain the desired dimer(s). The product can be analyzed and quantitatively determined by gas chromatography.

According to the present invention, since the Ziegler catalyst contains nickel chloride as the nickel component, the catalytic activity can be greatly increased. For example, the amounts of the expensive trialkylaluminum and hexafluoroisopropanol can be decreased, so that the cost of catalyst can be considerably reduced.

In addition, by the use of the active hydrogen-containing compound, the isomer distribution in the produced olefin dimers can be advantageously controlled.

PREFERRED EMBODIMENTS OF THE INVENTION

Practically and presently preferred embodiments of the present invention will be illustrated by the following Examples.

EXAMPLE 1

In a stainless steel 100 ml autoclave which had been evacuated, dried and filled with nitrogen, chlorobenzene containing 0.05 mmol of anhydrous nickel chloride (5 ml), chlorobenzene containing 0.05 mmol of tricyclohexylphosphine (0.5 ml) and isoprene (4 mmol, 0.4 ml) were added in this order and mixed. Then, chlorobenzene containing 0.25 mmol of triethylaluminum (0.25 ml) was added and the mixture was stirred while cooling with ice. To the ice-cooled mixture, chlorobenzene containing 0.75 mmol of 1,1,1,3,3,3-hexafluoroisopropanol (hereinafter referred to as "HFIP") (0.75 ml) was added while stirring, followed by stirring for 10 minutes. To the catalyst solution, absolute chlorobenzene (4.6 ml) was added and then propylene was injected in the autoclave to a pressure of 4 kg/cm² followed by stirring at 20° C. for 30 minutes.

After the reaction was completed, the reaction mixture was sampled under pressure and subjected to gas chromatography with using n-pentane as the internal standard. The results are shown in Table 1.

The reaction mixture after purging unreacted propylene was clear, and no deposit was found on the inner wall of the autoclave.

EXAMPLE 2

In the same manner as in Example 1 except that after the addition of the triethylaluminum solution, chlorobenzene containing 0.1 mmol of methanol (0.2 ml) was added and the mixture was stirred, and then the HFIP solution was added followed by stirring, the catalyst was prepared and the dimerization was carried out. The results are shown in Table 1.

The reaction mixture was clear, and no deposit was found on the inner wall of the autoclave.

EXAMPLES 3-6

In the same manner as in Example 1 but using the organic phosphorus-containing compound (0.05 mmol) shown in Table 2 in place of tricyclohexylphosphine, the catalyst was prepared and the dimerization was carried out.

The results are shown in Table 2.

TABLE 1

| Example No. | Effi- ciency[1] of catalyst | Selec- tivity[2] of dimers (%) | Selec- tivity[3] of DMBS (%) | Distribution of dimers (%) | | | | | | Isomeri- zation ratio[4] (%) |
|---|---|---|---|---|---|---|---|---|---|---|
| | | | | 2,3-di- methyl- 1-butene | 2,3-di- methyl- 2-butene | 4-methyl- 2-pentene | 2-methyl- 1-pentene | 2-pentene | 2-hexene | |
| 1 | 23.1 × 10³ | 69.2 | 77.7 | 5.1 | 72.6 | 6.5 | 1.8 | 14 | 0 | 93.4 |
| 2 | 17.4 × 10³ | 60.2 | 84.8 | 4.8 | 80 | 3.2 | 0.8 | 11.2 | 0 | 94.4 |

Note:
[1] Efficiency of the catalyst based on the converted propylene (C₃'). (Mole of converted propylene C₃')/(g-atom of Ni × time (hrs))
[2] A percentage (by mole) of the dimers based on converted propylene.
[3] A percentage (by mole) of 2,3-dimethylbutenes (DMBS) in the dimers.
[4] (2,3-dimethyl-2-butene/2,3-dimethylbutenes) × 100.

TABLE 2

| Example No. | Organic P-cont. compound | Efficiency of catalyst | Selectivity of dimers (%) | Distribution of dimers (%) | | | | | |
|---|---|---|---|---|---|---|---|---|---|
| | | | | 2,3-di- methyl- 1-butene | 2,3-di- methyl- 2-butene | 4-methyl- 2-pentene | 2-methyl- 1-pentene | 2-methyl- 2-pentene | 2-hexane |
| 3 | P(i-Pr)₃ | 20.8 × 10³ | 82.0 | 10.7 | 61.4 | 11.1 | 2.1 | 14.7 | 0 |
| 4 | P(n-Pr)₃ | 31.2 × 10³ | 85.6 | 2.7 | 38.2 | 11.9 | 5.1 | 42.2 | 0 |
| 5 | P(C₆H₅)₃ | 9.9 × 10³ | 89.6 | 1.5 | 21.2 | 12.4 | 0 | 64.9 | 0 |
| 6 | P(O-C₆H₅)₃ | 28 × 10³ | 90.9 | 3.4 | 32.7 | 15.3 | 6.4 | 42.1 | 0 |

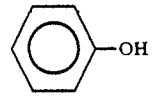

EXAMPLES 7–13

In the same manner as in Example 2 but using the active hydrogen-containing compound (0.1 mmol) shown in Table 3 in place of methanol, the catalyst was prepared and the dimerization was carried out.

The results are shown in Table 3.

TABLE 3

| Ex- am- ple No. | Active H- containing compound | Effi- ciency of catalyst | Yield of dimethyl- butenes (%) | Selectivity of dimethyl- butenes (%) |
|---|---|---|---|---|
| 7 | H₂O | 24 × 10³ | 48.3 | 80.6 |
| 8 | C₂H₅OH | 22.8 × 10³ | 53.4 | 81.2 |
| 9 | n-C₃H₇OH | 16.1 × 10³ | 48.8 | 79.9 |
| 10 | n-C₈H₁₇OH | 18.7 × 10³ | 44.9 | 80.4 |
| 11 | CH₂=CHCH₂OH | 21.5 × 10³ | 49.7 | 80.5 |
| 12 | C₆H₅—OH | 23.4 × 10³ | 48.2 | 80.5 |
| 13 | CH₃COOH | 15.5 × 10³ | 46.1 | 80.9 |

COMPARATIVE EXAMPLE 1

In the same manner as in Example 1 but using nickel naphthenate (0.05 mmol) in place of nickel chloride, 0.5 mmol of triethylaluminum and 1.5 mmol of HFIP, the catalyst was prepared and the dimerization was carried out.

The results are shown in Table 4.

COMPARATIVE EXAMPLE 2

In the same manner as in Example 1 except that, after the addition of isoprene, water (0.25 mmol, 4.5 μl) was added, then chlorobenzene containing 0.5 mmol of triethylaluminum (0.5 ml) and chlorobenzene containing 1.75 mmol of 2,4,6-trichlorophenol (1.75 ml) were added in this sequence followed by stirring for 15 minutes and the chlorobenzene (3.35 ml) was added, the catalyst was prepared and the dimerization was carried out.

The results are shown in Table 4.

COMPARATIVE EXAMPLE 3

In the same manner as in Comparative Example 2 but using 0.125 mmol of water, 0.25 mmol of triethylaluminum and 0.875 mmol of 2,4,6-trichlorophenol, the catalyst was prepared and the dimerization was carried out.

The results are shown in Table 4.

TABLE 4

| Compa- rative Example No. | Efficiency of catalyst | Yield of dimethyl- butenes (%) | Selectivity of dimethyl- butenes (%) |
|---|---|---|---|
| 1 | 18.7 × 10³ | 39.7 | 87.4 |
| 2 | 13 × 10³ | 42.6 | 70.1 |
| 3 | 3.1 × 10³ | 27.5 | 71.2 |

What is claimed is:

1. A process for preparing a dimer of a lower α-olefin comprising dimerizing α-olefin in the presence of a catalyst consisting essentially of
   (A) nickel chloride,
   (B) a trialkylaluminum,
   (C) at least one phosphorus compound selected from the group consisting of compounds of the formu- lae:

$$PR^1R^2R^3 \qquad (I)$$

$$R(NR^1{}_2)_3 \qquad (II)$$

and $$P(OR^1)_3 \qquad (III)$$

wherein $R^1$, $R^2$ and $R^3$ are the same or different and each an alkyl group, a cycloalkyl group or a phenyl group and (D) 1,1,1,3,3,3,-hexafluoroisopropanol.

2. The process according to claim 1, wherein the catalyst further comprises (E) at least one active hydrogen-containing compound of the formula:

$$R-OH \qquad (IV)$$

wherein R is a hydrogen atom, an alkyl group having 1 to 8 carbon atoms, an allyl group, an aryl group having 6 to 8 carbon atoms or an acyl group having 3 to 4 carbon atoms in an amount less than the equimolar amount to the trialkylaluminum.

3. The process according to claim 1, wherein the lower α-olefin is propylene.

4. The process according to claim 1, wherein the molar ratio of the trialkylaluminum (B) to nickel chloride (A) is from 2 to 500, the molar ratio of the phosphorus compound (C) to nickel chloride (A) is from 0.1 to 50, and the molar ratio of the 1,1,1,3,3,3,-hexafluoroisopropanol (D) to the trialkylaluminum (B) is from 0.2 to 10.

5. The process according to claim 2, wherein the molar ratio of the trialkylaluminum (B) to nickel chloride (A) is from 2 to 100, the molar ratio of the phosphorus compound (C) to nickel chloride (A) is from 0.1 to 20, the molar ratio of the 1,1,1,3,3,3-hexafluoroisopropanol (D) to the trialkylaluminum (B) is from 0.5 to 5, and the molar ratio of the active hydrogen-containing compound (E) to the trialkylaluminum (B) is from 0.1 to 0.8.

6. The process according to claim 2, wherein the molar ratio of the trialkylaluminum (B) to nickel chloride (A) is from 2 to 10, the molar ratio of the phosphorus compound (C) to nickel chloride (A) is from 0.1 to 2, the molar ratio of the 1,1,1,3,3,3-hexafluoroisopropanol (D) to the trialkylaluminum (B) is from 1 to 4, and the molar ratio of the active hydrogen-containing compound (E) to the trialkylaluminum (B) is from 0.2 to 0.6.

7. The process according to claim 1, wherein the concentration of the catalyst is from $10^{-5}$ to $10^{-1}$ mol/liter in terms of the concentration of the nickel component.

8. The process according to claim 1, wherein the trialkylaluminum (B) is triethylaluminum.

9. The process according to claim 1, wherein the phosphorus compound (C) is at least one selected from the group consisting of tricyclohexylphosphine, tri-iso-propyl-phosphine, tri-n-butylphosphine, tri-sec.-butyl-phosphine, triphenylphosphine and triphenylphosphite.

10. The process according to claim 9, wherein the phosphorus compound (C) is tricyclohexylphosphine.

11. The process according to claim 2, wherein the phosphorus compound (C) is at least one selected from the group consisting of tricyclohexylphosphine, tri-iso-propyl-phosphine, tri-n-butylphosphine, tri-sec.-butyl-phosphine, triphenylphosphine and triphenylphosphite.

12. The process according to claim 11, wherein the phosphorus compound (C) is tricyclohexlphosphine.

13. The process according to claim 2, wherein the active hydrogen-containing compound (E) is at least one selected from the group consisting of water, methanol, ethanol, n-propanol, octanol, allyl alcohol, phenol and acetic acid.

14. The process according to claim 13, wherein the active hydrogen-containing compound (E) is methanol.

* * * * *